United States Patent [19]

Richmond et al.

[11] Patent Number: 6,088,114

[45] Date of Patent: Jul. 11, 2000

[54] APPARATUS FOR USE IN DETERMINING MEAT TENDERNESS

[75] Inventors: Robert J. Richmond, Lacombe; Steven P. Nadeau, Guelph, both of Canada

[73] Assignee: Ontario Cattlemen's Association, Ontario, Canada

[21] Appl. No.: 09/297,909

[22] PCT Filed: Oct. 29, 1997

[86] PCT No.: PCT/CA97/00810

§ 371 Date: Jul. 1, 1999

§ 102(e) Date: Jul. 1, 1999

[87] PCT Pub. No.: WO98/20339

PCT Pub. Date: May 14, 1998

[30] Foreign Application Priority Data

Nov. 7, 1996 [CA] Canada ................................. 2189817

[51] Int. Cl.⁷ ..................................................... G01N 21/64

[52] U.S. Cl. ...................... 356/417; 250/461.1; 250/910

[58] Field of Search ..................................... 356/417, 317, 356/318; 250/458.1, 459.1, 461.1, 910

[56] References Cited

FOREIGN PATENT DOCUMENTS

| 0 402 877 | 12/1990 | European Pat. Off. . |
|---|---|---|
| 0 416 658 | 3/1991 | European Pat. Off. . |
| WO 92 21025 | 11/1992 | WIPO . |
| WO 93 24832 | 12/1993 | WIPO . |

OTHER PUBLICATIONS

Swatland, H.J.: "Dynamic Analysis of Electromechanical Data from a Hand–Held Meat Probe in Relation to Meat Structure", *Food Research International*, vol. 27, 1994, Canada, pp. 433–441.

Swatland, H.J.: "Objective Measurement of Physical Aspects of Meat Quality", *Department of Food Science and Animal & Poultry Science*, University of Guelph, Guelph, Ontario N1G2W1, Canda, pp. 65–74.

Swatland, H.J., "Analysis of Signals from a UV Fluorescence Probe for Connective Tissue in Beef Carcasses", *Computers and Electronics in Agriculture*, vol. 6, 1991, pp. 225–234.

Swatland, H.J.: "Bidirectional Operation of a UV Fluorescence Probe for Beef Carcass Connective Tissues", *Computers and Electronics in Agriculture*, vol. 7, 1992, pp. 285–300.

Swatland, H.J.: "An Anomaly in the Effect of Temperature on Collagen Fluorescence in Beef", *Food Research International*, vol. 26, 1993, Canada, pp. 271–276.

Swatland, H.J.: "Correlations of Mature Beef Palatability with Optical Probing of Raw Meat", *Food Research International*, vol. 28, No. 4, 1995, Canada, pp. 403–416.

Swatland, H.J.: "UV Fiber–Optic Probe Measurements of Connective Tissue in Beef Correlated with Taste Panel Scores for Chewiness", *Food Research International*, vol. 28, No. 4, 1995, Canada, pp. 23–30.

Swatland, H.J.: "An Effect of Connective Tissue on the Taste Panel Tenderness of Commercial Prime Beef Detected with a UV Fiber–Optic Probe", *Department of Food Science and Animal & Poultry Science*, University of Guelph, Guelph, Ontario N1G 2W1, Canada.

*Primary Examiner*—F. L. Evans
*Attorney, Agent, or Firm*—Alston&Bird LLP

[57] ABSTRACT

A portable apparatus for assessing meat quality, comprises: a hand-held instrument comprising a main body having at one end a hollow meat probe for penetrating meat, an optic fibre extending through the main body and terminating at a window at the distal end of the probe. The main body has a probe position sensing device for sensing position as the probe enters and exits the meat. A carrier pack is adapted for mounting on an operator. The pack comprises a fluorimetry unit having a source of ultraviolet radiation, a power source and a microcontroller/processing unit. A user interactive communications device is on the main body and a cable interconnects the main body and the carrier pack. The cable transmits electronic data between the interactive communication device and the microcontroller/processor unit and ultraviolet radiation output and fluorescent light input between the probe window and the fluorimetry unit.

31 Claims, 5 Drawing Sheets

APPARATUS FOR USE IN DETERMINING MEAT TENDERNESS

SCOPE OF THE INVENTION

This invention relates to an apparatus which may be used in carrying out predictions of meat quality based on optical properties. A system which consistently predicts meat quality, particularly in respect of tenderness, would be of significant benefit to the consumer, and as well to the packing house and to the farmer. The apparatus for use in determining meat tenderness involves probing the meat with a probe which emits radiation to excite connective tissue to fluoresce. The probe is designed to pick up and transmit such fluorescence. The apparatus may be used with a depth of penetration sensing device and dedicated software to provide an indication of meat quality. The probe may also be used to detect other optical properties which correlate with meat quality based on a distinctive pattern of fluorescent peaks.

BACKGROUND OF THE INVENTION

The principle of connective tissues in meat fluorescing when exposed to a particular radiation wavelength has been known for some time as described by Swatland, H. J. *Objective Measurement of Physical Aspects of Meat Quality*, Reciprocal Meat Conference Proceedings, Vol. 42, 1989. Initial investigations in the development of a probe, which is capable of both exciting and collecting fluorescence from connective tissue in meat, are described in Swatland, H. J. *Analysis of Signals from a UV Fluorescent Probe for Connective Tissue in Beef Carcasses*, Computers and Electronics in Agriculture (6, 1991) 225:234 and *Bidirectional Operation of a UV Fluorescent Probe for Beef Carcass Connective Tissues*, Computers and Electronics in Agriculture (7, 1992) 285:300, both of Elsevier Science Publishers B. V. Amsterdam. The original probe was an adaptation of a fat depth probe used by the Danish Meat Research Institute in Denmark for measuring the depth of fat on pig carcasses. The probe was adapted by the use of an optical fibre which was inserted in the device. The fibre was cut at an angle so that the interface optics were asymmetrical. Exciting radiation was supplied in the optic fibre from a 100 watt short arc mercury source directed through a heat absorbing filter, a red attenuation filter and a dichroic mirror. Light peaking at 365 nanometers was directed into the proximal end of the optic fibre with a microscopic objective. Fluorescence from the connective tissues in contact with the optical fibre of the probe was measured through the dichroic mirror at the proximal end of the fibre with a flat response silica detector and a radiometer. The dichroic mirror was used as a chromatic beam splitter to separate the outgoing excitation light at 365 nanometer from the incoming fluorescent emission at a wavelength considerably greater than 365 nanometer. A depth measurement device for measuring the depth to which the probe was plunged into the carcass was provided either by an optical shaft encoder to trigger photometer measurements at set increments through the carcass, or a continuously variable analog device, such as a potentiometer. The operation of the potentiometer can be affected by temperature.

The positioning of the glass optic fibre in the probe was also suggested, instead of being cut at an angle, of being slightly bent or rounded in conjunction with a plurality of additional thin fibres as described in the article by Swatland, H. J., *Bi-directional Operation of a UV Fluorescence Probe for Beef Carcass Connective Tissues* Computers and Electronics in Agriculture 7(1992) 285:300. The use of the multiple fibres around the glass optic fibre was to gather additional information in respect of shape of the connective tissue as the probe passed by the connective tissue.

Extensive analysis of the collected fluorescence from use of the meat probe is described in several papers by Swatland in Food Research International which include *Correction for Baseline Drifting in Probe Measurements of Connective in Beef*, Food Research International 26, 1993 371:374; *An Anomaly in the Effective Temperature on Collagen Fluorescence in Beef*, Food Research International, 26, 1993 271:276 and *Correlations of Mature Beef Palatability with Optical Probing of Raw Meat*, Food Research International, Vol 28, No. 4, pp 403–416, 1995. Swatland also published with others in Swatland et al., *An Effective Connective Tissue on the Taste Panel Tenderness for Commercial Prime Beef Detected with a UV Fibre Optic Probe* (cite to be inserted) and *UV Fibre Optics Probe Measurements of Connective Tissue in Beef Correlated with Taste Panel Scores for chewieness*, Food Research International, Vol 28. No. 1, pp 23–30, 1995. Although considerable work has been done in the area of correlating the fluorescent signature of meat when probed with the apparatus to provide an indication of meat tenderness, the widespread use of the technology has been limited by several factors. These include the prohibitive costs and the inconvenience associated with the concept that a large, cumbersome device was necessary to protect delicate electronic components from the harsh environment typically found in a slaughterhouse. In addition, many factors may cause toughness in meat including the distance between fibres, the thickness of the fibre and the type of fibre. For example, Type I and Type III collagen have different fluorescent emission spectra. While the probes described in the prior art were capable of detecting major septa of connective tissue, the distance between the point of data collection and processing in conjunction with the lack of dedicated software resulted in a signal to noise ratio that was insufficient to detect very thin fibres. Thus, little information could be gathered about the relative role of narrow high fluorescence versus a wide septum of low fluorescence nor was it possible to accurately detect the spacing of the peaks (i.e. many small peaks close together). The current invention addresses these problems.

SUMMARY OF THE INVENTION

The invention provides a portable device for probing meat, such as beef, pork, lamb and horsemeat, in the overall process of assessing meat quality. The probe emits ultraviolet light which causes connective tissue to fluoresce during either insertion or removal of the probe from the meat. The fluorescent signal is then collected and analyzed while preferably the operator is standing beside the carcass. The apparatus may then be adapted to feed back information to the operator predicting the quality of the meat based on signature and comparison to standards, such that the carcass can be classified and the operator can move onto the next carcass. The complete apparatus optionally including data analysis is portable obviating the need for bulky equipment and delayed data processing and analysis. The apparatus is capable of achieving a signal-to-noise ratio far superior to prior art types of probes and which is sufficient to detect varying thicknesses of connective tissue and more particularly very thin connective tissue fibres which correlate with a measure of meat quality.

In one aspect of the invention, the apparatus comprises a hand held unit which has a meat piercing probe protruding at one end. Within the probe there is an optic fibre which emits ultraviolet radiation through a window near the tip of the probe. Associated with the handheld unit there is a device for measuring the depth of penetration of the probe into the meat. The handheld unit also provides for interactive communication between the operator and the software responsible for analysis of the both the fluorescent data and the depth of penetration data. This hand held unit is connected to a carrier pack via a conduit capable of transmitting electronic data between the interactive communication device and the microcontroller/processor. This cable also transmits ultraviolet radiation output and visible light input between the fluorimetry unit within the carrier pack and the probe window.

In accordance with a preferred aspect of the invention, the user interactive communication device is ideally manually activated via an alphanumeric keypad. In other aspects of the invention, it may be activated by a touch screen or a bar code reader. In a particularly preferred aspect of the invention, the manually activated interactive communication device has a visual display which is a liquid crystal display (LCD) readout. In accordance with another aspect of the invention, the visual display comprises a light emitting diode (LED) readout. In a particularly preferred aspect of the invention, the visual display provides online feedback to the operator for immediate classification of the carcass. This classification may be achieved by printing of indicia unique to the carcass on a label for attachment to or otherwise associated with the carcass.

In a further preferred aspect of the invention, the handheld unit has a centrally located pistol-grip-like handle.

And in yet a further aspect of the invention, the handheld unit has a hollow meat probe for piercing meat. The meat piercing probe has bidirectional cutting surfaces and also extending along and within it an optic fibre. The fibre is made of plastic and bent in a smooth curve at 90° to terminate at a window at the distal end of the probe. Within the main body of the handheld unit, the optic fibre extends through a hollow protective sheath. This fibre is capable of transmitting ultraviolet radiation output and visible light input.

In a further aspect of the invention, the handheld unit has a depth of penetration sensing device which may have a meat contacting foot which is adapted to slide along the long axis of the probe as the probe enters the meat.

In a preferred aspect of the invention, the meat contacting foot is connected with a position encoder which travels, as the probe is inserted or withdrawn, over a plastic strip which has signaling elements embedded in it.

In a further aspect of the invention, the carrier pack may be transported by the operator via a backpack like mechanism involving over the-shoulder straps, via a belt attached around the waist, via an over-one 10 shoulder strap or via a briefcase-like carrier. The carrier pack provides the means of focusing UV light on the end of the optic fibre. Additionally, it collects and transmits the incoming fluorescent signal. Within the carrier pack, the microcontroller/processing unit analyses the fluorescent data and correlates the fluorescent signature with a standardized readout to provide feedback to the operator pertaining to the predicted meat quality.

In a further aspect of the invention, the handheld unit and carrier pack are connected via a cable which is non-metallic and resistant to water, oil and most chemicals.

BRIEF DESCRIPTION OF THE DRAWINGS

Preferred embodiments of the invention are described with respect to the drawings, wherein:

FIG. 8 (a) shows the fluorescent signature obtained with probes of the prior art when in (b)the probe penetrates the meat and (c) shows the corresponding peaks obtained with the apparatus of this invention.

DETAILED DESCRIPTION OF THE PREFERRED EMBODIMENTS

The portability of the device is achieved in the use of an intelligent handheld instrument for probing the meat, a pack which functions as a home base for generating and collecting electromagnetic radiation indicative of the fluorescent signature of the meat as well as data transmission to and from the intelligent handheld instrument. Communication between the two components is provided by way of a communications and electromagnetic radiation transmission cable. The portability of the device provides for carcass side probing of the meat to collect data in respect of the fluorescent signature of the meat and optionally to analyze instantaneously such data to provide the operator with feedback in respect of meat quality.

Figure 1:
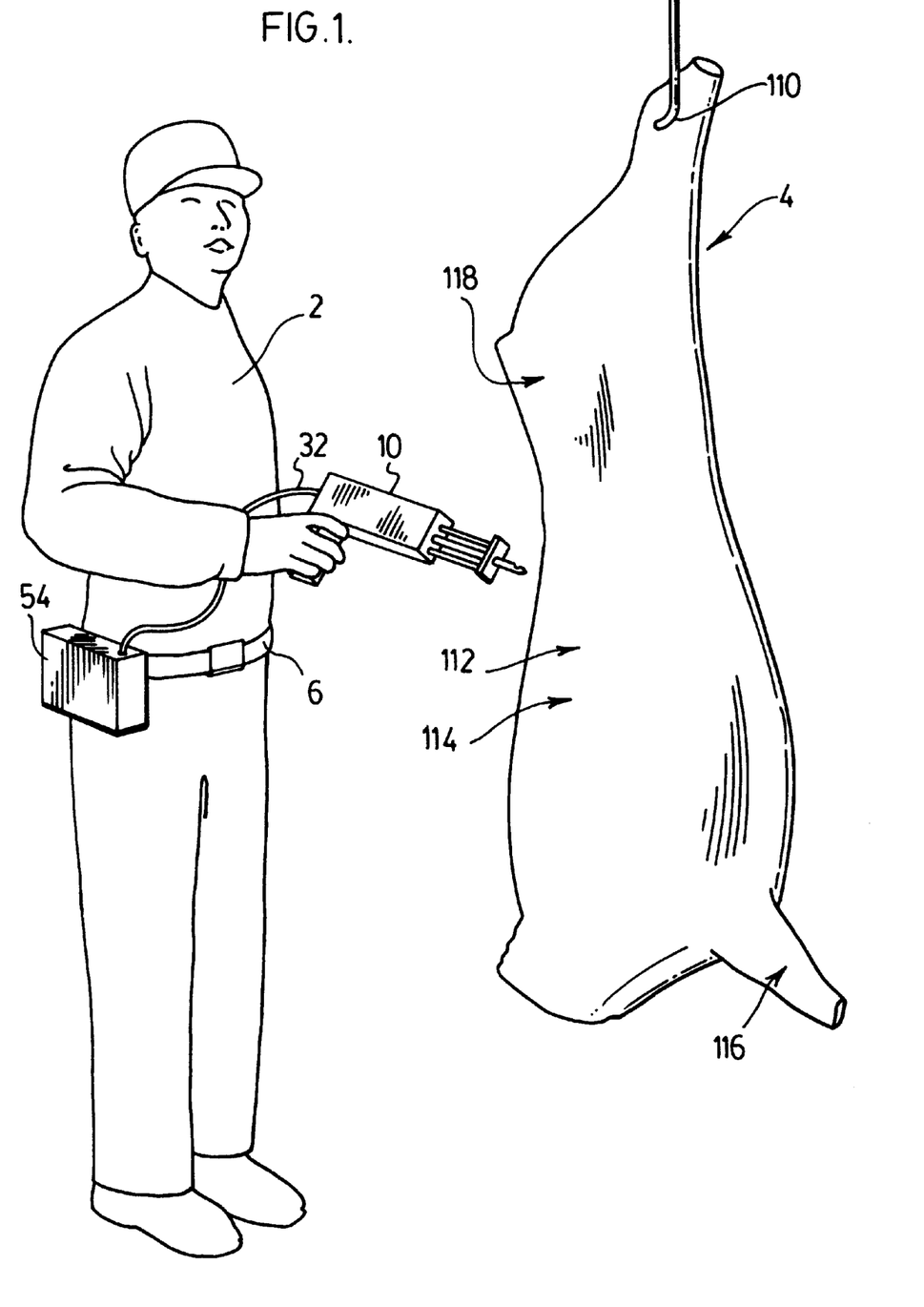
FIG. 1 is a perspective view of the entire apparatus in accordance with one aspect of the invention.

FIG. 1 illustrates an operator 2 using the portable apparatus to pierce a beef carcass. The invention comprises a handheld unit 10, a carrier pack 54 and a cable 32 interconnecting the two. The carrier pack 54 may be carried by the operator 2 via means of a belt 6 secured around the waist.

Figure 2:
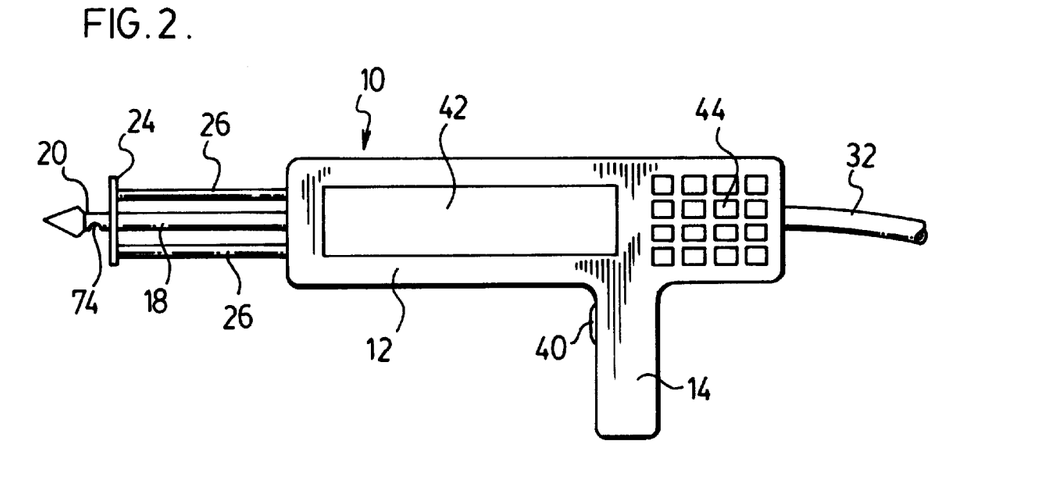
FIG. 2 is a perspective view of the hand held unit.

The handheld unit is shown in further detail in FIG. 2. It has at one end a protruding meat piercing probe 18 from which ultraviolet radiation is emitted through a window 74 at the distal end and also has associated with it a meat contacting foot 24 for determining depth of penetration of the probe. The handheld unit also provides an interactive communication device which, in this embodiment, includes keypad 42 and visual display 44. A finger activated switch 40 is used to signal whether the probe is penetrating or withdrawing from the meat. It is understood that the handheld unit 10, although shown for use by hand, may also be used in conjunction with robotics. Such robotic use of the apparatus may result in the apparatus having different provisions for carrying out various functions such as measurement of depth of penetration. It is further understood that the handheld instrument, although shown in conjunction with a separate carrier pack, may contain the elements found therein and provide for a single handheld apparatus.

The handheld unit 10 has a main body portion 12 with a pistol grip 14 centrally located to enhance balance. The pistol grip 14 has a switch 40 that may be used to signal to the controller/processor unit that the penetration of the probe into the meat has stopped and that the next step will be removal of the probe from the meat. It is understood that incorporation of linear actuators or the like would obviate the need for such a switch. The handheld unit 10 has at one end a meat piercing probe 18 which has an optic fibre extending along and within it. The optic fibre 34 terminates at a window 74 at the distal end 20 of the long axis of the probe. The meat piercing tip has bidirectional cutting surfaces to ensure smooth passage of the probe both on the way in and on the way out. In order to measure the depth of penetration, a stainless steel foot 24 surrounds the probe 26 which extend into ted on rods 26 which extend into the main body of the gun. Movement of the rods into the main body 12 as will be described with respect to FIG. 3, establishes the position/depth of penetration of the probe. It is understood that other modes of determining position could be utilized. The position data can be correlated with the fluorescent readout to provide an objective measure of connective tissue thickness. The handheld unit 10 is connected to the carrier pack by a conduit cable 32.

An interactive communication device mounted on the side of the handheld unit provides a means for inputting data such as carcass number, sampling site, time, date and the like and receiving the input from the microcontroller/processor unit including status of the system, status of data collection, status of data analysis and, perhaps as well, an analyzed result. The interactive communication device may be manually activated by the use of switches, an alphanumeric keypad, a touch screen or the like or it may be activated by reading a bar code. Feedback to the user may be via a visual display such as a series of lights, a liquid crystal display (LCD), a light emitting diode or the like and may also include printing of a label or tag for association with a carcass. In the preferred embodiment, a visual display unit 42 and user operated alphanumeric keypad 44 are located on the side of the main body 12. During use the keypad and visual display unit provide the user a communication link with the associated software. The keypad may be used to enter carcass number and sampling site and to initiate the microcontroller. As shown in FIG. 1, a side of beef which may be hung by the hind leg 110 may have four desired locations for probing meat tenderness; namely, 112, 114, 116 and 118. Before probing the carcass, the keypad 44 is used to enter the corresponding carcass number and probe site. Hence the fluorescence signature for each position is correlated with the respective carcass. It is appreciated that this same technique may be used to assess tenderness of individual cuts of meat such as single cuts. The visual display 42 provides menu options and time/date information and indicates to the operator the status of the controller, whether there was good data collection, that data was sent and acceptable, errors, input required and the like. Additional modes of feedback may include printing of indicia unique to the carcass on a label for affixing to or associated with the carcass. Thus, the interactive communication device provides the operator with the online or "carcass-side" analysis required to make a predictive judgment on the quality of the meat being assessed and provides for rapid classification of a carcass. The invention has the potential to be connected into the plant system for automatic sorting of classified carcasses.

Figure 3:
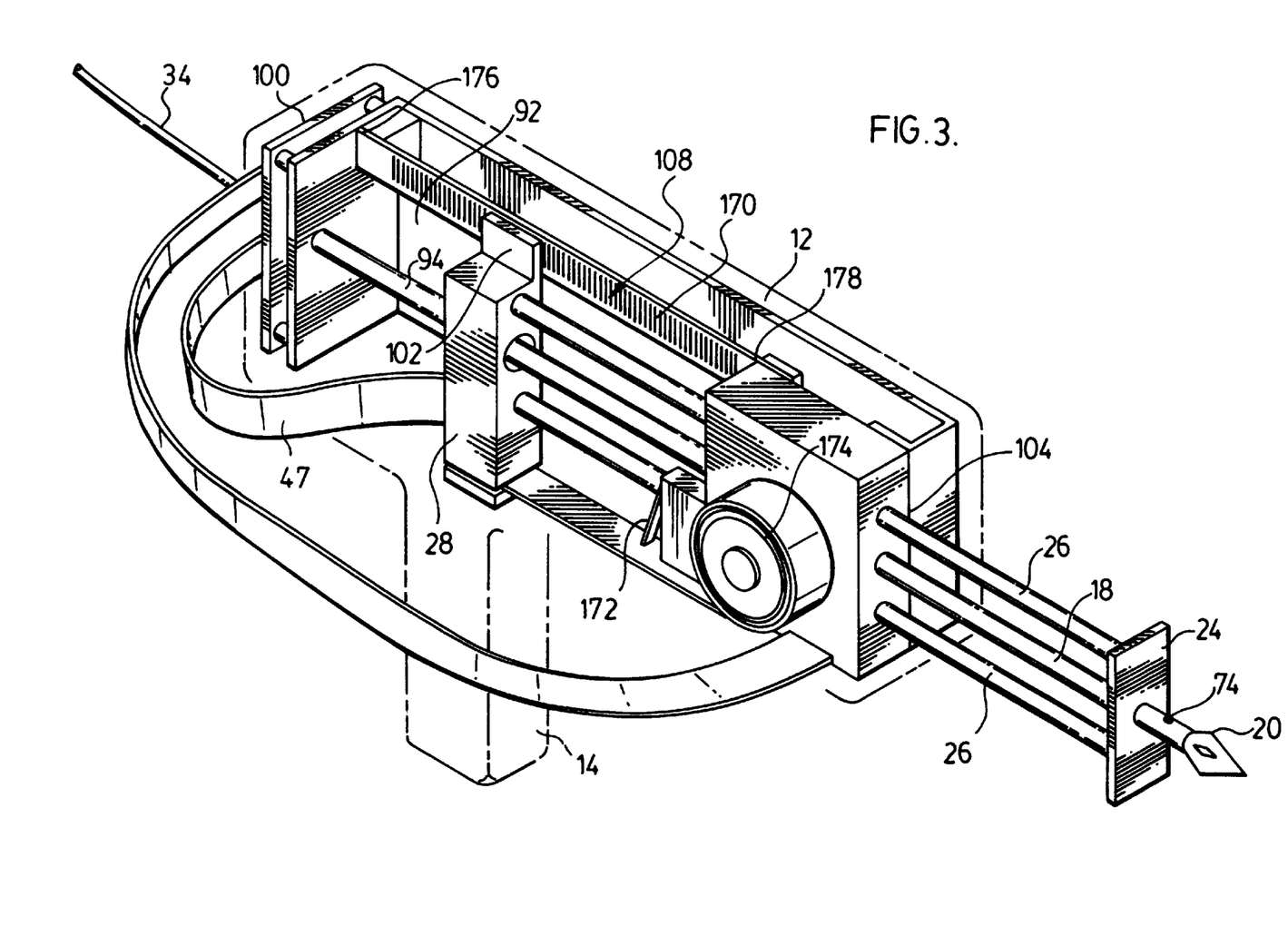
FIG. 3 is a perspective view of the handheld unit with the casing removed.

As shown in FIG. 3, the main body has a hollow interior which houses a protective sheath 94 which may be a continuation of the probe wall 18 and which may be supported by appropriate devices (not shown) within the hollow body 92. The circuit board 100 picks up a signal via cable 47 from a position encoder 102 which is used to determine at any moment the depth of penetration of the probe tip 20 into the meat. The meat contacting stainless steel foot 24 is connected to the rods 26 which extend through the face 104 of the body portion 12. The rods 26 are connected to a slider mechanism 28 which, in turn, is connected to the position encoder 102. There is a limit switch 172 which defmes the "home" or "O" position on the encoder strip 108 when the rods 26 attached to the flat foot 24 are fully extended beyond the face 104 of the apparatus 10. A coiled spring 174 resiliently biases the flat foot 24 to the fully extended position. As the foot 24 recedes into the main body 12, during meat testing, the coil spring stores energy to return the foot to extended position as the probe is withdrawn from the meat. During use, the rods 26 recede into the hollow body portion 12 and moves the slider mechanism 28, whereby the position encoder 102 is moved along an encoded strip 108 which is securely fastened within the unit at fixed supports 176 and 178, to transmit correspondingly the extent to which the tip and, in particular, the window 74 has moved beyond the face of the foot element 24. The encoded strip 108 may be provided with encoding marks 170 at intervals less than every 50 micrometers so that the exact position of the encoder 102, as it moves along the strip 108, may be determined by the number of pulses transmitted from the encoder 102 through the circuit board 100 to the microcontroller 62. Such encoding unit, for the depth of penetration, is not temperature sensitive and provides a viable system for correlating the fluorescent peaks with the position of the probe window 74 in the meat. It is understood that other modes of determining the position of the probe within the meat are contemplated, such as a rack and pinion drive for an encoded wheel.

Figure 4:
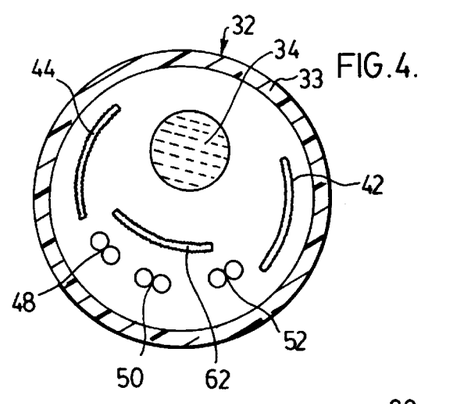
FIG. 4 is a cross-section through the conduit cable.

As shown in FIG. 1, the handheld unit 10 is connected to the carrier pack 54 via a conduit cable 32. This "cable" may be a single cable or a conduit enclosing different types of cable. In whichever form, this cable transmits i) electronic data between the operator and the microcontroller/ processor unit, and ii) ultraviolet radiation output and fluorescent light input between the probe and the fluorimetry unit within the carrier pack In the preferred embodiment, the conduit cable 32 shown in FIG. 4 carries not only the optic fibre 34 but also the visual display ribbon cable 42, the keypad ribbon cable 44, the microcontroller cable 62 and various electrical cables 48, 50, 52. The conduit 32 is non-metallic and provides protection against crushing and rupture due to repeated flexing. It permits the operation of the apparatus in the environmentally hostile environment often found in packing plants. The tubing 33 retains its flexibility at a broad temperature range and is resistant to oil, water and most chemicals. Nonmetallic fittings which use a locknut and sealing o-ring provide a liquid and oil tight connector for each component.

Figure 5:
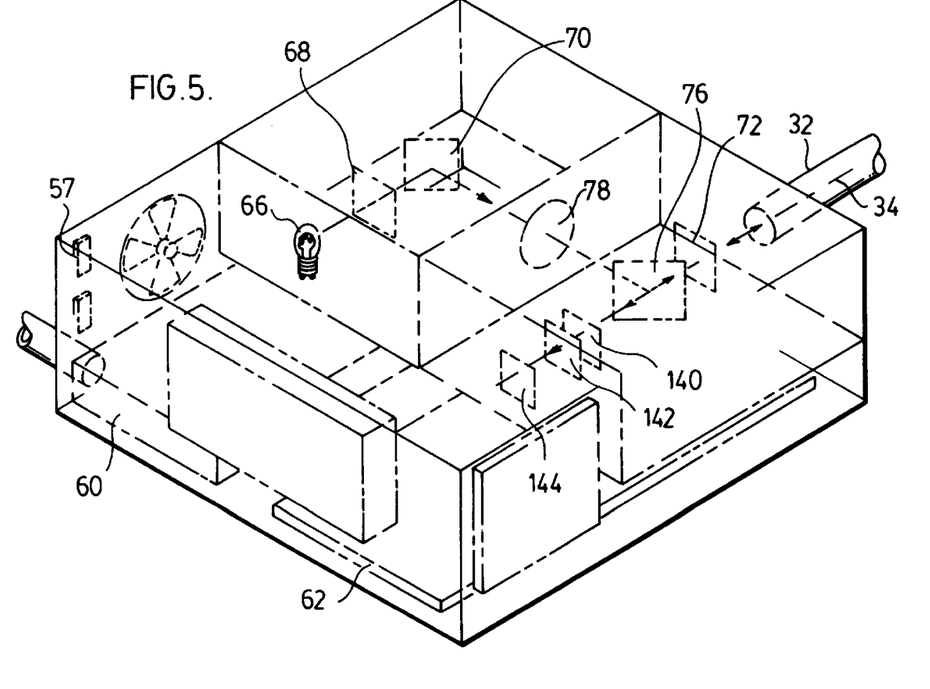
FIG. 5 is a perspective top view of the carrier pack with the casing removed.

The carrier pack 54, shown in FIG. 5, may be transported by the operator either via a backpack like mechanism involving over the shoulder straps, via a belt attached around the waist, via an over-one-shoulder strap or via a briefcase-type of carrier. The carrier pack comprises the fluorimetry unit, the power supply and the microcontroller/processor unit. Within the fluorimetry unit there are means to focus ultraviolet radiation onto the end of the optic fibre and means to collect and translate the incoming fluorescent signal into a readable format. It is understood that with continued miniaturization, the functions performed by components within the carrier pack may be achievable by components small enough to fit inside the handheld unit, thus providing for a self contained handheld apparatus. In the preferred embodiment, the optic fibre 34 passing through the conduit 32 is connected to the carrier pack as shown in FIG. 5, where the light source is powered by the power supply 60 which is preferably rechargeable by electrical plug 57. The light source 66 supplies UV radiation in cable 34 which is at the selected wavelength less than 400 nanometers and preferably in the range of 360–370 nanometers. This radiation excites collagen to fluoresce as the probe penetrates the meat, where the emitted fluorescence is collected and transmitted through the optic fibre 34 back to the photodetector 144. The fluorescent intensity is detected and, in turn, transmitted to the microcontroller/processor 62. The microcontroller/processor is programmed to analyze the collected fluorescence relative to the depth of penetration of the probe to give an indication of the size and number of connective tissues in the meat being penetrated. Correlating this fluorescent signal with an established standard allows the software to predict the overall tenderness of the meat section being probed to allow the meat packer, processor or marketer to decide on how that particular portion of meat will be processed or marketed. Additionally, the unit has the potential to be connected into the plan system to signal through a hook-up 180 for automatic sorting of carcasses.

As shown in FIG. 5, a source of UV light may be provided by a Welch Allyn metal halide solar arc lamp 66. The radiation from the lamp passes through a focusing lens 68 which selects the desired wavelength in the range of 365 nanometers. This focused radiation then travels to a 45° angled UV mirror 70 which allows the UV radiation to be reflected into a UV transmitting filter 78. The UV transmitting filter prevents visible radiation from entering the detector side. Once the radiation is filtered it travels to a 45'angled UV mirror 76 which steers the UV light at a 90° angle into a focusing lens 72 which further modifies the light for transmission along the optic fibre 34. The optic fibre transmits the UV light to the opening or window 74 formed in the side of the probe 18 as described in FIG. 6 so as to direct the UV radiation laterally of the probe. Collagen in the vicinity of the opening 74 fluoresces where the emitted fluorescent radiation is collected at opening 74 and transmitted back through the optic fibre 34. As shown in FIG. 5, the returning fluorescent light travels through the focusing lens 72 and then travels to the 45° angled UV mirror 76. The mirror 76 removes any reflected UV light and allows the visible light to pass straight through to the long pass filter 140 which prevents residual UV light from passing through and only allows the visible fluorescent light to pass through. The visible light passes through a focusing lens 142 and converges onto the photodetector 144. The intensity of the fluorescent signal may be detected by a photomultiplier tube in the detector 144 which converts visible light into an electric signal for further processing. Software is provided in the microcontroller 62 to analyze the peaks in the fluorescent signal and where those peaks are matched for insertion and withdrawal of the probe to allow peak numbers, heights and half-widths to be determined. An example of how the microcontroller board 62 analyzes the data is as follows. Firstly, the fluorescent light is detected by a photodetector 144 and enters the microcontroller board 62. A photomultiplier, located on the microcontroller board, translates the fluorescent light into a signal which is able to be inputted into a software program running within the microcontroller board. The software program, running within the microcontroller board, takes the depth measurement (from the position encoder board) and the signal (produced by the photomultiplier) as inputs. In the preferred embodiment of the present invention, after receiving the input data, the program proceeds to match the inputs to a predetermined look-up table stored within the memory of the microcontroller. After finding a match, the program reads a second stored value (also stored in the look-up table) corresponding to the matched data. This second stored value is then returned to the user as a description of the toughness or tenderness of the tested meat. Such information is then processed to correlate the fluorescent signature of the tested section of meat with its anticipated tenderness when consumed.

Figure 6:
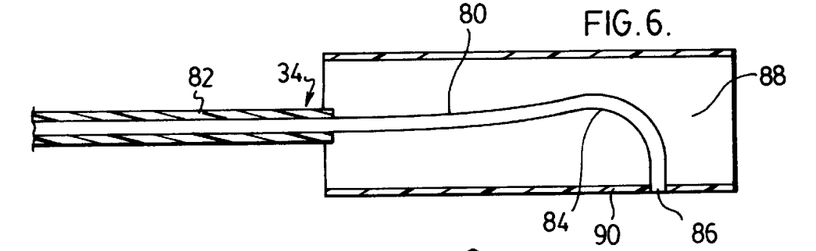
FIG. 6 is a exploded view through part of the handheld unit showing the positioning of the optic fibre in the opening of the probe.

FIG. 6 provides further details of the probe 18 with the optic fibre 34 therein. The fibre "per se" 80 has a protective coating 82. The optic fibre 80 is preferably of plastic which allows the fibre to be curved smoothly at 90° in region 84 so that the end of the fibre 86 projects radiation laterally of the longitudinal axis 88 of the probe 18. Preferred plastic fibres such as the ESKA Mega are available from Poly-Optical Products Ltd. of California and General Fibre Optics, Inc. of New Jersey. Such plastic fibres comprises a 1 mm diameter jacketed communications grade plastic fibre. Such fibres are durable, flexible and have low noise to signal ratios. Suitable material may be applied at window 90 to fix the end 86 of the fibre in position. A transparent lens or the like may be used to protect the fibre terminal end in the window 90. Such material does not interfere with the optics of the fibre 80. Plastic fibre provides a superior signal to noise ratio and has greater durability properties compared to optic fibre of glass, such as silica. The fibre length has been significantly reduced in the portable aspect of the invention and has a numerical aperture capable of providing a superior signal to noise ratio in excess of 100:1.

Figure 7:
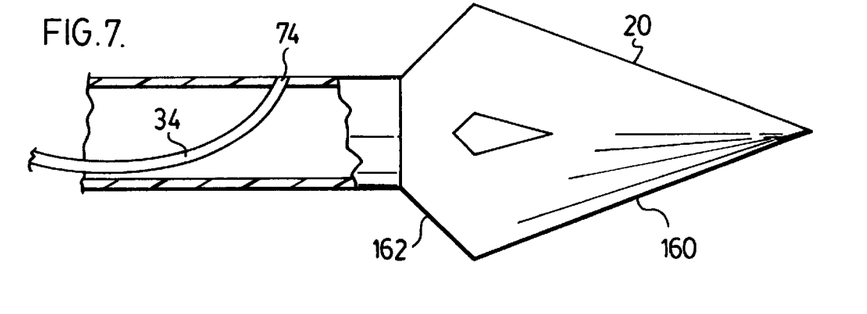
FIG. 7 is a side view of the piercing end of the probe.

FIG. 7 is an improved piercing tip for the probe 18. The optic fibre 34 terminates in the opening 74 behind the tip 20. The tip 20 is made from a sharpened tungsten carbide material and presents very sharp bidirectional cutting surfaces 160 and 162 which cleanly penetrate the muscle fibre and avoid compression of the meat so that the collagen, as the probe penetrates the meat, is not moved and hence varying the relative positioning of the fluorescent peaks of FIG. 8. On withdrawal, surfaces 162 also cleanly slice the meat to permit and facilitate withdrawal of the tip should it be rotated during the withdrawal step. The clean severing of the meat also avoids damaging the meat or in any way spoiling the meat appearance for market.

Figure 8A:
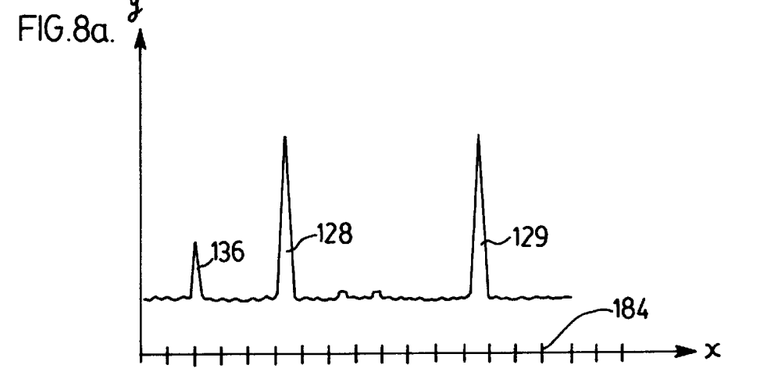
Figure 8B:
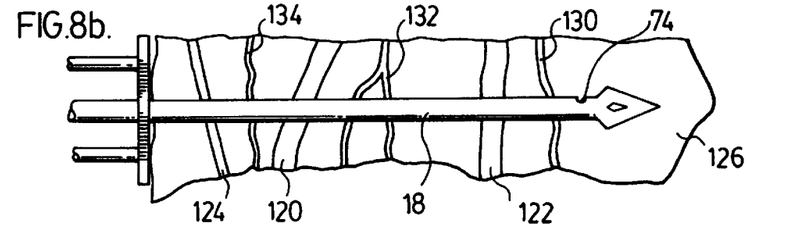
Figure 8C:
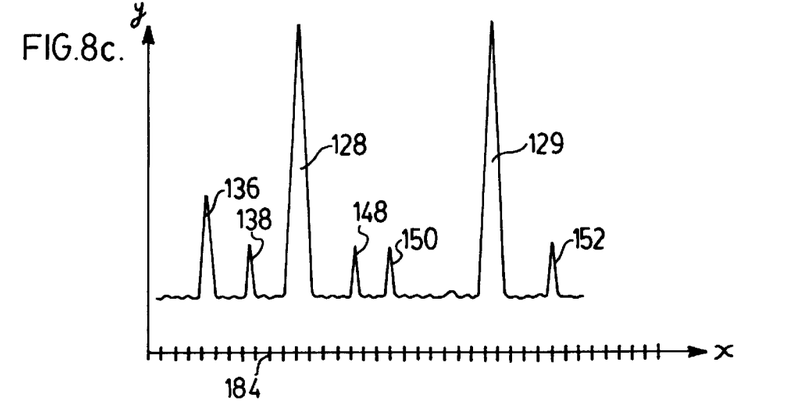

The vast difference in the sensitivity achieved by previous probes, as compared to the current invention, is shown in FIG. 8. FIG. 8a shows the fluorescent signature obtained with the previous type of probe when the probe penetrates the meat, as shown in FIG. 8b. FIG. 8c illustrates the significant difference in respect of peaks obtained with the apparatus of this invention. The y-axis indicates the fluorescent intensity while the x-axis correlates with the depth of penetration. Also along the x-axis, the sampling frequency of the two probes is indicated by the black tick marks 184. The frequency sampling in FIG. 8c may be at least double that of FIG. 8a.

As the probe 18 is inserted through a section of meat 126, as shown in FIG. 8b, the window or end of the optic fibre 74 projects the UV radiation into the meat. As the meat sample is penetrated and, for example, the opening 74 passes through a major septa of connective tissue as indicated at 120 or 122, very significant fluorescent peaks are observed at 128 and 129 shown in FIGS. 8a and 8c. Some smaller connective tissue fibres at 124 give rise to corresponding peak 136 in FIGS. 8a and 8c. However, while very thin connective tissue fibres such as at 130, 132 and 134 in FIG. 8b are not detected in the fluorescent signature 8a generated by the probe described in the prior art, the probe of the current invention is able to these strands as shown by the peaks 138, 148, 150 and 152 in FIG. 8c.

The fluorescence pattern is an indicator of the amount of collagen in each piece of meat and hence the greater the sensitivity of detection the better it can be correlated with anticipated tenderness of the meat when cooked. As shown in FIG. 8, the apparatus of the current invention provides afar superior analysis. Such a sensitive determination of connective tissue is achievable only through the significantly increased signal-to-noise ratio provided by this invention in concert with an enhanced sampling frequency. The ability to collect more data and therefore detect finer gradations facilitates carcass-side analysis of meat quality. Thus, this aspect is much easier to use than previous models and additionally provides a vastly enhanced fluorescent signature.

Various aspects of the invention have been described in detail. It is appreciated that variations may be made thereto without departing from the spirit of the invention or the scope of the appended claims.

What is claimed is:

1. A portable apparatus for assessing meat quality, comprising
    i) a hand-held instrument comprising a main body having at one end a hollow meat probe for penetrating meat, an optic fibre extending through said main body and terminating at a window at the distal end of the probe, said main body having a probe position sensing device for sensing position as the probe enters and exits the meat;
    ii) a carrier pack adapted for mounting on an operator, said pack comprising a a fluorimetry unit having a source of ultraviolet radiation, a power source and a microcontroller/processing unit;
    iii) a user interactive communications device on said main body;
    iv) a cable interconnecting said main body and said carrier pack, said cable transmitting
        a) electronic data between said interactive communication device and said microcontroller/processor unit, and
        b) ultraviolet radiation output and fluorescent light input between said probe window and said fluorimetry unit.

2. A portable apparatus of claim 1 wherein said user interactive communication device is manually activated.

3. A portable apparatus of claim 2 wherein said user interactive communication device has an alpha-numeric keypad.

4. A portable apparatus of claim 2 wherein said interactive communication device has a touch-screen.

5. A portable apparatus of claim 2 wherein said interactive communication device has a bar code reader.

6. A portable apparatus of claim 2 wherein said interactive communication device has a visual display.

7. A portable apparatus of claim 6 wherein said interactive communication device has an liquid crystal display (LCD) panel.

8. A portable apparatus of claim 6 wherein said interactive communication device has a light emitting diode (LED) panel.

9. A portable apparatus of claim 6 wherein said visual display is capable of providing on line feedback to enable immediate classification of a carcass.

10. A portable apparatus of claim 9 wherein said classification is achieved by printing of indicia unique to the carcass on a label for affixing to or association with the carcass.

11. A portable apparatus of claim 6 wherein said instrument is gun-shaped having a pistol grip handle.

12. A portable apparatus of claim 11 wherein said handle is centrally located.

13. A portable apparatus of claim 1 wherein said probe has a piercing tip having bidirectional cutting surfaces.

14. A portable apparatus of claim 1 wherein said probe has an optic fibre extending along and within the probe an terminating at a window at the distal end of the long axis of the probe shaft.

15. A portable apparatus of claim 14 wherein the fibre is made of plastic and bent in a smooth curve at 90° to said window.

16. A portable apparatus of claim 14 wherein said optic fibre extends through a hollow protective sheath supported within said main body.

17. A device of claim 15 wherein said fibre is capable of transmitting UV radiation output and receiving visible light input.

18. A portable device of claim 17 wherein said depth of penetration sensing device has a meat contacting foot which is adapted for reciprocal movement along said probe.

19. A portable device of claim 18 wherein said foot is connected with a slider mechanism on which is attached a position encoder that travels over a plastic strip, having signaling elements embedded thereon, upon penetration of the probe into the meat or withdrawal thereof to provide an incremental measure of probe position.

20. A portable device of claim 18 wherein said carrier pack has shoulder straps for transportation on the back of the operator.

21. A portable device of claim 18 wherein said carrier pack is transported by the operator by means of a belt attached around the waist.

22. A portable device of claim 20 wherein said power source has rechargeable batteries.

23. A portable device of claim 22 wherein said fluorimetry unit provides a means of focusing the ultra-violet radiation on the end of said optic fibre and means of collecting and translating the incoming fluorescent signal.

24. A portable device of claim 23 wherein said fluorimetry unit additionally comprises means of focusing light, means of reflecting ultraviolet light, means of selecting a specific wavelength and means of collecting fluorescent signals.

25. A portable device according to claim 24 wherein said means of collecting fluorescent signals is a photomultiplier tube.

26. A device according to claim 22 wherein said cable comprises a nonmetallic conduit with enclosed tubing being resistant to water, oil and most chemicals, said cable interconnecting the said probe unit and the said carrier pack via fittings which are non-metallic and produce a liquid and oil tight connection.

27. A portable device of claim 22 wherein said microcontroller/processor has software implemented within capable of receiving and analysing fluorescent data and means of correlating said data with sampled peak width as determined by increment of penetration.

28. A device of claim 27 wherein said microcontroller/processor is capable of providing a sampling frequency which, in concert, with an optic fibre of selected characteristics in terms of numeric aperture, length and refractive index provides a signal to noise ratio which enables detection of the thinnest connective tissue that correlates with a measure of toughness, tastiness, chewiness or juiciness.

29. A device of claim 28 wherein said optic fibre has a numeric aperture greater than 0.47.

30. A device according to claim 28 wherein said optic fibre has a length less than 3.5 meters.

31. A device according to claim 28 wherein said sampling frequency is greater than 2000 transects per second.

* * * * *